United States Patent
Steffler

Patent Number: 5,156,602
Date of Patent: Oct. 20, 1992

[54] HYDROPHOBIC FILTER PROTECTOR FOR WOUND DRAINAGE SYSTEM

[75] Inventor: Mike W. Steffler, Kalamazoo, Mich.

[73] Assignee: Stryker Corporation, Kalamazoo, Mich.

[21] Appl. No.: 578,015

[22] Filed: Sep. 5, 1990

[51] Int. Cl.⁵ ............................................. A61M 1/00
[52] U.S. Cl. .................................... 604/319; 604/317
[58] Field of Search ...................... 604/318, 320, 319; 220/202, 203, 204, 205, 206, 209, 216

[56] References Cited

U.S. PATENT DOCUMENTS

| | | | |
|---|---|---|---|
| 3,768,478 | 10/1973 | Fertik et al. | 604/320 |
| 4,111,204 | 9/1978 | Hessel | 604/320 |
| 4,228,798 | 10/1980 | Deaton | 604/49 |
| 4,465,485 | 8/1984 | Kashmer et al. | 604/320 |
| 4,487,606 | 12/1984 | Leviton et al. | 604/319 |
| 4,561,558 | 12/1985 | Richman et al. | 220/203 |
| 4,561,868 | 12/1985 | von Reis et al. | 55/319 |
| 4,569,674 | 2/1986 | Phillips et al. | 604/119 |
| 4,655,754 | 4/1987 | Richmond et al. | 604/323 |
| 4,826,494 | 5/1989 | Richmond et al. | 604/323 |

Primary Examiner—David J. Isabella
Assistant Examiner—Elizabeth M. Burke
Attorney, Agent, or Firm—Flynn, Thiel, Boutell & Tanis

[57] ABSTRACT

Apparatus for collecting body liquids from a patient comprises a reservoir connectible to a patient to collect body liquids therefrom. A filter in the reservoir is interposed between an air vent and a liquid receiving zone in the reservoir. The filter faces generally upward within a chamber which is disposed near the top of the reservoir and is closed to the reservoir except for at least one restrictive orifice communicating between the reservoir and the top of the chamber. The restrictive orifice opens to the reservoir near the top of a boss upstanding from the top of the chamber and opens to the chamber at a location radially outboard of the filter. A barrier depends from the top of the chamber radially between the restrictive orifice and filter. A bowl supports the filter and has a bottom spaced above the bottom of the chamber to define a liquid receiving sump therebetween. The bowl has a peripheral wall upstanding from the bottom wall thereof and rising above the top of the filter at a location radially inboard of the barrier. To gain contact with the filter, liquid from the reservoir must rise above the top of the chamber sufficient to overflow the boss, pass downward through the restrictive orifice in the boss pass the barrier and fill the sump sufficient to overflow the top of the bowl peripheral wall.

13 Claims, 4 Drawing Sheets

HYDROPHOBIC FILTER PROTECTOR FOR WOUND DRAINAGE SYSTEM

FIELD OF THE INVENTION

This invention relates to a hydrophobic filter protector for a wound drainage system.

BACKGROUND OF THE INVENTION

The Assignee of the present invention manufacturers vacuum wound drainage systems and autotransfusion systems in which a reservoir for body liquids is connected to the body of a patient to remove liquids therefrom and also is connectable to a vacuum source for producing a subatmospheric pressure in the reservoir and thereby drawing liquids from the patient's body into the reservoir. In the case of a wound drainage system, liquids, including blood, irrigation liquid, fatty liquids, etc. are drawn from a wound (usually a surgical wound) into the reservoir for later discard. In the case of an autotransfusion system, blood is drawn from a patient into the reservoir for subsequent reuse.

In both instances, it is known to provide, at the connection of the vacuum source to the reservoir, a means to allow air from the reservoir to be drawn into the vacuum source but prevent liquids, liquid droplets, etc. from the reservoir from being drawn into and contaminating the vacuum source. A particularly advantageous known device for doing this is a hydrophobic filter, namely a filter which readily passes gases therethrough but blocks passage therethrough of liquids and liquid droplets. While various hydrophobic filter materials are known, one effective hydrophobic filter material is sold under the name Goretex TM, manufactured by W. L. Gore Assoc. located at Elkton, Md.

The hydrophobic filter allows the reservoir to fill with liquid while allowing gases, such as air, to be removed continuously or at any time, to maintain a subatmospheric pressure in the reservoir. When the liquid level rises to the level of the filter, the filter prevents liquid from the reservoir from contaminating the vacuum source, and the liquid blinds the hydrophobic filter.

However, the present applicant has noted that such systems in actual use may blind or substantially blind the hydrophobic filter prematurely, before the reservoir is filled with liquid. For example, the reservoir may be tipped or jiggled, resulting in splashing of droplets or larger quantities of the liquid therein on the hydrophobic filter face. Also, foam on the top surface of the liquid may wet the hydrophobic filter face in whole or part. In this, and other ways, the hydrophobic filter face may become prematurely partially or fully blocked by a liquid reaching and then adhering to it.

Attempts have been made in the past to prevent premature contact of liquids with a filter in reservoirs of the above type by providing a filter support incorporating a tortuous path through which air and any liquid components must pass before reaching the filter. For example, U.S. Pat. Nos. 4,561,868 (von Reis et al.) and earlier U.S. Pat. No. 4,228,798 (Deaton) both disclose a filter support within such a reservoir, in which the filter support includes a cover spaced below a downward facing filter for forcing the flow of fluid downwardly away from the filter prior to flowing in the opposite direction (upward) through the filter. The cover includes an upward opening cup having a bottom wall spaced below the filter and side walls extending upwardly and radially outwardly from the bottom wall. Radially within the upwardly opening cup is a centrally located annular wall pierced by plural, relatively large, closely circumferentially distributed windows. Fluids from the interior of the reservoir, to reach the filter, must pass through an S-shaped sinuous path, namely upward to the rim of the side wall of the cup, then downwardly along the sloped interior side walls of the cup and then radially inward through the windows in the annular wall within the cup and then upward to the downward facing filter. The flow through the filter is upward.

However, in the patents above discussed, the cross-sectional area of the liquid path into the cup is relatively large. Further, the cross-sectional area of the windows is relatively large as well. Thus, a brief but substantial tilting of the partially filled reservoir could fill the cup member with liquid and subsequent agitation of the reservoir could cause a portion of this trapped liquid to reach up into contact with the underside (the input side) of the filter. This is particularly true in von Reis whose structure is compact vertically to minimize the room it takes within the reservoir. Thus, even before the cup is entirely filled with liquid, such liquid may be able to contact the underside of the filter and partially or fully block it. In Deaton, the filter is spaced further above the cup but the sinuous path structure which is vertically space consuming and extends a substantial distance down into the reservoir, as compared with the diameter of the sinuous path structure. Thus, for the same filter area, the Deaton sinuous path structure is vertically substantially more space consuming than that of von Reis (and indeed that of the present invention).

The objects and purposes of the present invention include provision of apparatus for protecting, from unwanted liquid contact, a gas/liquid separating filter in a body liquid collection receptacle, and more particularly in the outlet of such receptacle to a subatmospheric pressure source, in which portions of the apparatus in initial contact with liquid from the reservoir are arranged to allow such liquid to drain back into the reservoir rather than accumulate in the vicinity of the filter, in which a restrictive orifice is interposed in the gas path through the apparatus from the reservoir to the filter, in which the input face of the filter may be upward facing and thus face away from the collected pool of liquid in the reservoir, in which the apparatus forms a part of the support and containment for the filter and is compact, particularly in its vertical dimension, and is adapted to lie in fixed relation immediately under the cover of the reservoir.

Further objects and purposes of the invention will be apparent to persons acquainted with apparatus of this general type upon reading the accompanying description and viewing the accompanying drawings.

SUMMARY OF THE INVENTION

Apparatus for collecting body liquids from patients including a reservoir, the reservoir being connectable to a patient to collect body liquids. A filter in the reservoir is interposed between an air vent and a liquid receiving zone in the reservoir. A structure in the reservoir protects the filter from contamination by the liquid in the reservoir.

DETAILED DESCRIPTION

While the present invention is applicable to other apparatus for collecting body liquids, it is convenient to disclose it as an improvement in an autotransfusion apparatus 10 (FIG. 1) marketed by the Assignee of the present invention. An autotransfusion apparatus similar to that shown at 10, but without the present invention, is disclosed, for example, in application Ser. No. 305,901 filed Feb. 2, 1989 and assigned to the Assignee of the present invention. The protector embodying the present invention is also usable, for example, in vacuum wound drainage systems, for example of the kind disclosed in U.S. Pat. Nos. 4,826,494, 4,655,754, and 4,569,674 assigned to the Assignee of the present invention.

Protectors embodying the present invention are, of course, also usable in other apparati, particularly of the kind for collecting body fluids in a medical or surgical setting.

Figure 1:
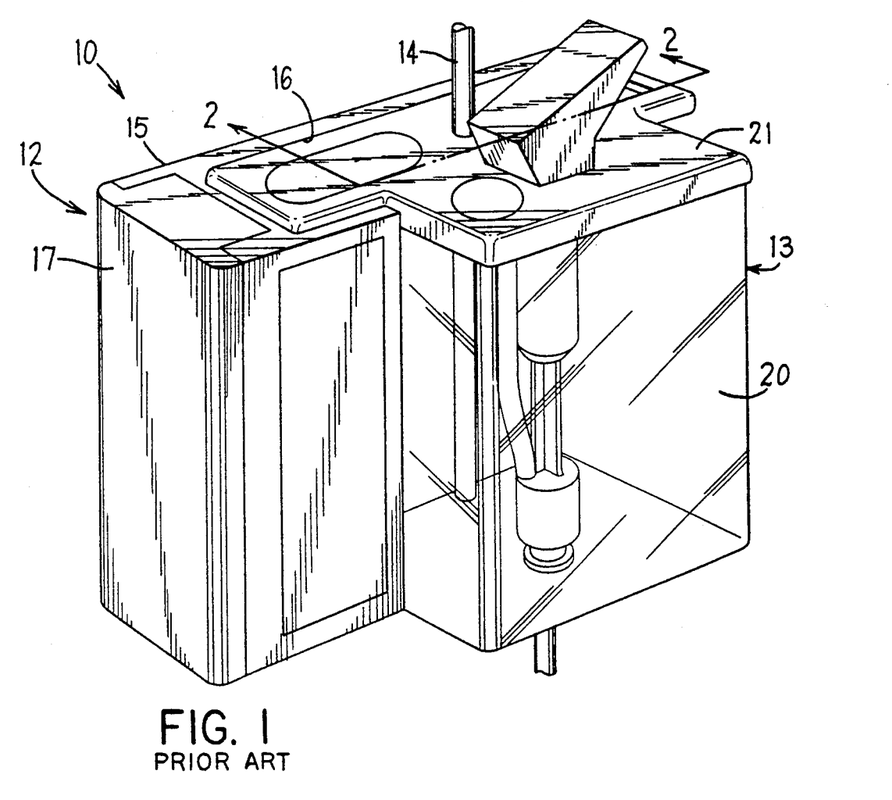
FIG. 1 is a pictorial view of a prior art autotransfusion apparatus to which the present invention is applied.

The particular autotransfusion apparatus illustrated in FIG. 1 includes a base unit 12 and a drain reservoir 13. The drain reservoir is releasably securable to the base unit for partial evacuation to a subatmospheric (negative) pressure. A drain tube 14 is used to connect the reservoir 13 to a patient for receiving body liquid therefrom. The reservoir 13 is disconnectable from the base unit 12 without impairing the negative pressure within the reservoir 13. Thus, the reservoir 13 can be used for vacuum drainage both while connected to the base unit 12, as well as after disconnection from the base unit. The reservoir (with or without the base unit) can be carried by a patient or on a mobile patient support (not shown) and moved therewith from place to place.

The base unit 12 comprises a housing 15 having a forwardly facing groove 16 into which the reservoir 13 is downwardly insertable. The housing 15 releasably supports a battery pack 17 and a vacuum source (not shown). In the embodiment shown, the base unit 12 incorporates a motor driven (not shown) by the battery pack 17 and driving a vacuum pump (not shown) to which the reservoir 13 is coupled for evacuation, upon inserting of the reservoir 13 into the groove 16 in the base unit 12. The contents of the base unit 12 and the manner in which it is operated to evacuate the reservoir 13 is disclosed in the aforementioned patents assigned to the Assignee of the present invention and needs no further description here.

Figure 2:
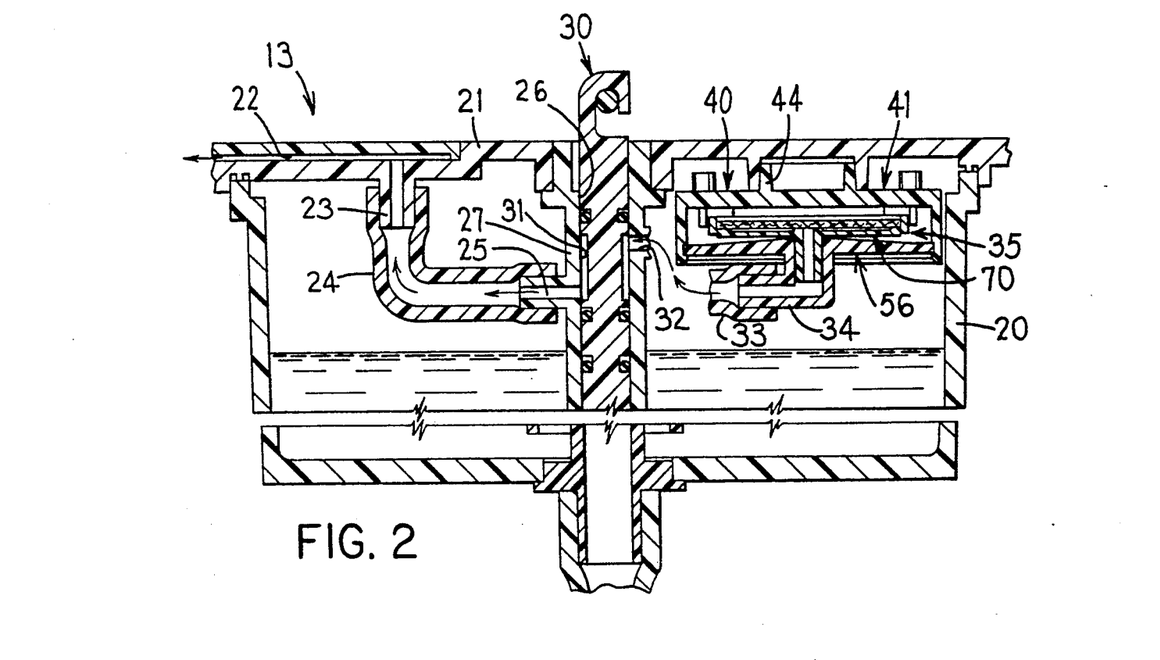
FIG. 2 is a fragmentary central cross-sectional view of the FIG. 1 autotransfusion apparatus.

The reservoir 13 comprises an upward opening bottle 20, the top of which is closed by a cover 21.

A vacuum, or suction, passage 22 (FIG. 2), connectable to the vacuum source (not shown) in the base unit 12, extends laterally rightwardly (FIG. 2) in the cover 21 and communicates with a nipple 23 which depends from the cover 21 into the interior of the bottle 20. A flexible tube 24 couples the nipple 23 to a further nipple 25 which in turn communicates with a vertical valve bore in a vertical valve guide 27 which fixedly depends from the cover 21 in the reservoir 13. A vertically movable valve member 30 is provided with an annular groove 31 which, in one position (the position shown) of the valve member 30 communicates the nipple 25 through a lateral passage 32 in the valve guide 27 and thence through a flexible tube 33 to a further nipple 34 which in turn communicates with the outlet side of a hydrophobic filter unit 35.

To the extent above described, the apparatus is generally similar to that disclosed in aforementioned U.S. application Ser. No. 305,901 of February, 1989, assigned to the Assignee of the present invention. The apparatus above described at 23-33 could be simplified by elimination of the valve guide 27 and valve member 30 and direct coupling of the nipple 23 to the nipple 34 through a suitable extension of the tube 24, 33, if the present invention was desired to be used in a wound drainage reservoir, for example, the kind shown in mentioned U.S. Pat. No. 4,826,494 assigned to the Assignee of the present invention.

In any event, the apparatus above described with respect to FIGS. 1 and 2 is merely disclosed as one example of various types of apparatus to which the present invention can be applied.

Turning now to structure more specifically involving the present invention, attention is directed to FIGS. 3-7. The hydrophobic filter unit 35 is associated with a protector 40 (FIGS. 3 and 4) which comprises a protective member 41. The protective member 41 comprises a substantially horizontal deck 42 having a circular perimeter from which fixedly depends a skirt-like annular peripheral wall 43. The peripheral wall 43 is conveniently cylindrical. An annular wall 44 coaxially and fixedly upstands from the deck 42.

The protector 40 (FIG. 3) is fixed to and depends from the underside of the cover 21. In the embodiment shown, the top edge of the upstanding annular wall 44 extends nearly up to the underside of the cover 21. An annular shell 51 integrally depends from the cover 21 and is sized and located such to snugly and frictionally telescope over the upstanding annular wall 44 of the protective member 41. The annular shell 51 thus positively laterally locates the protective member 41 with respect to the cover 21. The depending annular shell 51 is taller than the upstanding annular wall 44 and so contacts the deck 42, the height of the protective member 41 thus being determined by abutment of the depending annular shell 51 against the top of the deck 42. The annular wall 44 and shell 51 are adhesively bonded fixedly to each other to fixedly locate the protective device 41 with respect to the cover 21.

Figure 7:
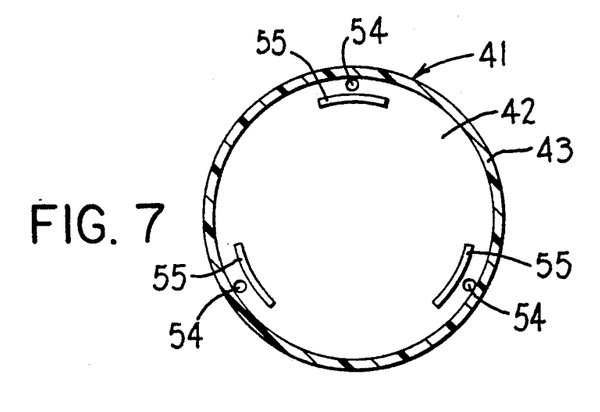
FIG. 7 is a reduced fragmentary sectional view substantially taken on the line 7—7 of FIG. 3.

The protective device 41 includes upstanding bosses 53, here three in number. The bosses 53 fixedly extend up from the deck 42 and the tops of the bosses 53 are about half way in height between the underside of the cover 21 and the top of the deck 42. The bosses 53 each have a central through bore 54 downward therethrough from the top thereof downward through the deck 42 to open through the bottom face of the deck as seen in FIG. 7. The through bores are very small in diameter compared to the overall diameter of the protective member 41, for example a .06 inch diameter through bore 54 for an overall 1.47 inch diameter protective member 41. Circumferentially spaced barriers 55 fixedly depend from the underside of the deck 42 immediately radially inboard of the respective through bores 54. The barriers 55 are each circumferentially substantially wider than the diameter of the respective through bore 54 adjacent thereto. For example, in the embodiment shown, such circumferential barrier extent is about .32 inch. The barriers 55 extend downward about one half the depth of the skirt-like peripheral wall 43 of the protective member 41.

Figure 4:
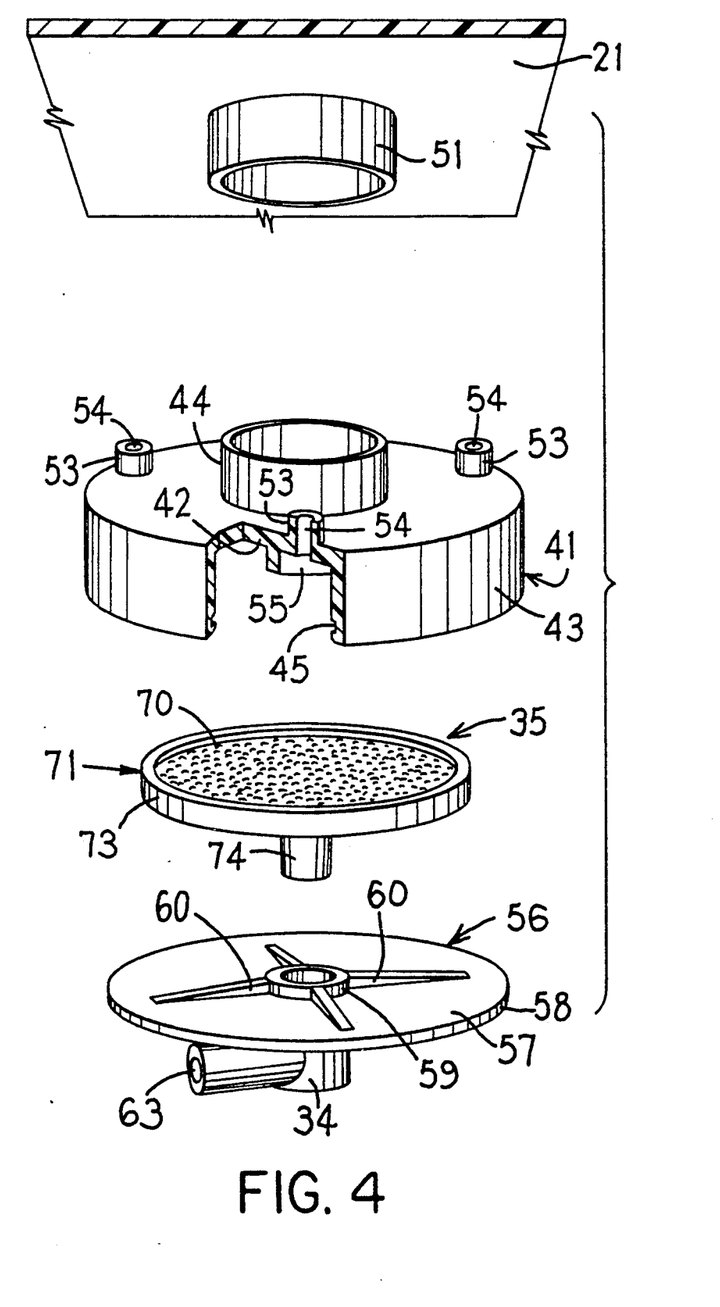
FIG. 4 is a fragmentary, exploded, pictorial view showing portions of the protector of FIG. 3 with a portion thereof broken away.
Figure 5:
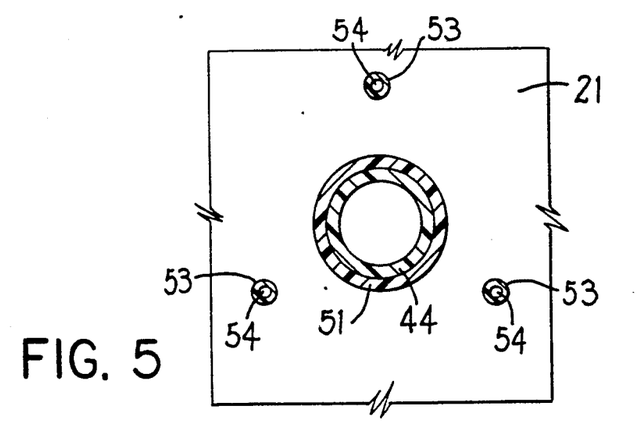
FIG. 5 is a reduced fragmentary sectional view substantially taken on the line 5—5 of FIG. 3.
Figure 6:
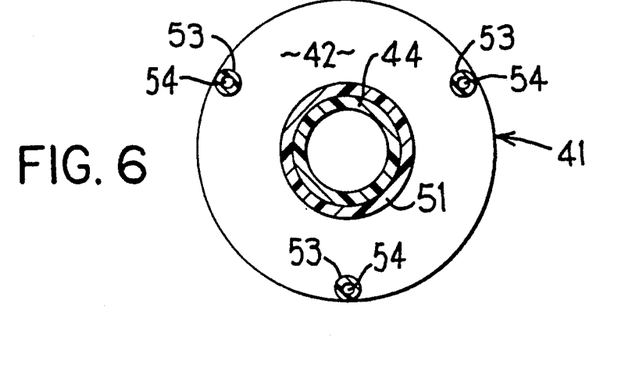
FIG. 6 is a reduced sectional view substantially taken on the line 6—6 of FIG. 3.

The protector 40 includes a substantially horizontal bottom member 56 (FIG. 4). The bottom member includes a substantially horizontal bottom wall 57. The bottom member has a fixed upstanding central hub 59 from which radiate plural (here four), circumferentially spaced anti-slosh ribs 60 fixed atop the bottom wall 57. In the embodiment shown, the outer peripheral edge 58 of the bottom wall 57 snap fits fixedly into an internal peripheral groove 45 in the lower portion of the peripheral wall 43 of the protector member 41, and is permanently fixed therein by adhesive bonding.

The above mentioned nipple 34 is, in the embodiment shown, substantially L-shaped and depends fixedly and integrally from the bottom wall 57 of the bottom member 56. The nipple 34 has an internal passage 63 that communicates upward through the hub 59 with a filter chamber 64 (FIG. 3) defined by the bottom wall 57, deck 42 and the peripheral wall 43.

Figure 3:
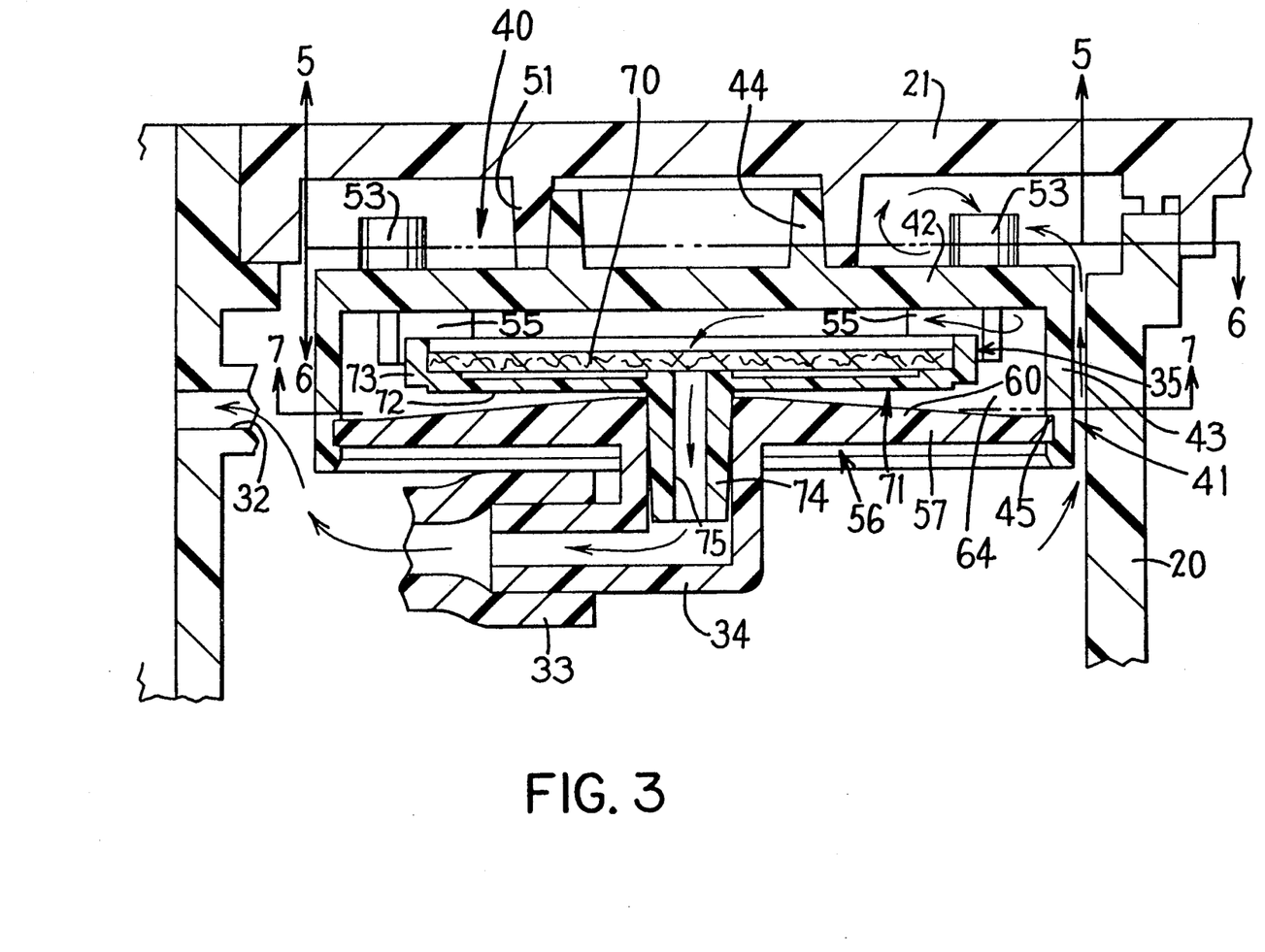
FIG. 3 is an enlarged fragment of FIG. 2 showing, in central cross section, a filter and filter protector according to the present invention.

The filter unit 35 is conventional and comprises a flat circular piece of hydrophobic filter material (for example, the above-mentioned Gortex TM brand material supported in a shallow, circular, upward opening bowl 71 having a flat bottom wall 72 which seats on the hub 59 of the bottom member 56 and a short upstanding peripheral wall 73. A hollow stem 74 is fixed to and depends from the central portion of the bottom wall 72 and is snugly received in the top of the passage 63 in the nipple 34. The stem 74 has a vertical through opening 75 communicating from the portion of the bowl beneath the filter material 70 with the outlet portion of the passage 63 of the nipple 34. The filter material 70 is seated in the bowl 71 in such manner that gases within the chamber 64 must flow downward through the filter material 70 to escape through the nipple 34.

The bowl 71 is coaxially spaced above the chamber bottom wall 57 and below the deck 42. The barriers 55 are spaced circumferentially around the bowl 71 and are located radially snugly outboard of the peripheral wall 73 of the bowl.

The above described members 21, 41, 56 and 71 are preferably of suitable rigid molded plastics material, for example polycarbonate.

OPERATION

It is conventional to draw liquid from the patient by means of the drain tube 14 into the reservoir 13 by reason of a subatmospheric pressure within the reservoir. The subatmospheric pressure may be stored following disconnection of the reservoir 13 from a vacuum source (for example, in the embodiment shown, by removal of the reservoir 13 from the base unit 12). Alternatively, the reservoir 13 may remain connected to the vacuum source (as shown in FIG. 1, for example). A subatmospheric pressure is induced in the reservoir 20 by suction therefrom of air, in FIG. 2 through the path 22-25, 31-34 and through the bottom of the hydrophobic filter unit 35. Thus, air within the reservoir is drawn downward through the hydrophobic filter material 70 and out through venting means here exemplified by such path 22-25, 31-34.

When the reservoir 20 has entirely filled with liquid, substantially to the underside of the cover 21, liquid will flood over the bosses 53 and run, downward through the holes 54. Thereafter, such liquid floods the chamber 64 to above the peripheral wall 73 of the bowl 71 (FIG. 3) and thus floods and blocks the top surface of the filter material 70. In this way, the filter material 70 fulfills its conventional purpose of preventing drawing of patient body liquids through the path 31-34 and 25-22 into the vacuum source in the base unit 12. This avoids contaminating such vacuum source and leaves it useful for other patients at a later time. Thus, the present invention permits this conventional purpose to be accomplished when the reservoir 20 has completely filled with liquid and can no longer be expected to draw further liquid from the patient.

It is, however, before the reservoir 20 is entirely filled with liquid, namely when the reservoir is only partially filled with liquid, that Applicant's inventive device served as a primary purpose, namely that of preventing blocking of the hydrophobic filter material 70 by contact with liquid in the reservoir. It is when the reservoir 20 is partially filled with liquid that the greatest risk of such premature blocking of the hydrophobic filter material 70 exists. This risk is increased when during drawing of air from the reservoir to a vacuum source and when the liquid in the reservoir is foaming, or is splashing due to agitation of the reservoir. Such agitation is usually unintended and accidental, but may occur, e.g. as a result of moving of the patient and the associated reservoir 13 and base unit 12 from place to place, rough handling of the reservoir 20, dropping of the reservoir 20, etc.

Sufficient agitation could cause droplets of liquid to fly up from the surface of the liquid as high as the cover 21. Momentary substantial tipping of the reservoir may cause liquid to momentarily contact a portion of the cover 21. Absent the protector 40, portions of the liquid might drop onto and blind the top of the filter material 70. However, the protector 40 forms an effective defense against such contact.

More particularly, liquid falling on the top of the deck 42 tends to merely run off without rising to the elevated tops of the bosses 53 upstanding from the deck. Because the top area of the bosses 53 is very small compared to the top area of the deck 42, only a very small proportion of liquid falling on the deck 42 would fall upon the top of the bosses 53 and have an opportunity to drain down through the holes 54 therein. Moreover, the cross-sectional area of the holes 54 is small compared to the area of the top of the bosses 53, so that a substantial portion of liquid falling on top of the bosses 53 would tend to simply drain down the outer side walls thereof rather than entering the holes 54. Thus, the likelihood of liquid entering the holes 54 is low and the amount of liquid capable of entering such holes 54 in the relatively short period of time in which liquid may be present near the tops of such holes, would be small, even if the partly filled reservoir is subjected to unusual amounts of agitation.

Any liquid running down through a given one of the holes 54 would tend, due to gravity, to fall to the bottom of the chamber 64, underneath the bowl 71 and thus not come into contact with the upward facing filter material 70, because of the spacing of the bottom 72 of the bowl above the bottom wall 57 of the chamber 64 and also because of the upward projecting peripheral wall 73 of the bowl. Further, any liquid emerging from the bottom of the through holes 54, is blocked even during substantial agitation of the reservoir 20, from moving radially inward over and then falling on top of the filter material 70 by the adjacent barrier 55 interposed radially between the bottom of the hole 54 and the bowl peripheral wall 73.

In view of the relatively large volume of the chamber 64, and placement of a large portion of that volume below the top of bowl peripheral wall 73, even severe agitation of the reservoir 20 and/or severe tilting of the reservoir over a relatively long period of time is unlikely to allow enough liquid to enter the chamber 64 to fill same to the extent necessary to overflow the top of the peripheral wall 73 and thereby flood the filter material 70. This is particularly true in view of the relatively large cross-sectional area of the chamber and the relatively great height to which the chamber would have to fill to overflow the top of the bowl peripheral wall 73, as compared to the very small cross-sectional area of each through hole 54 and the small number of such through holes 54. Thus, the present invention makes it very difficult to block the filter with liquid with the reservoir only partly filled even while a vacuum is being drawn in the reservoir 20. The likelihood of blocking is the same, not less.

Because of the large difference in viscosity of air and any other gases removed from the reservoir by the vacuum source, and the liquid drawn into the reservoir from the patient, the relatively small total cross-sectional area of the through holes 54 is adequate for rapid removal of air from the reservoir 13 by the vacuum source in the base unit 12 and consequent reduction of the interior of the reservoir 13 to a desired subatmospheric pressure.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. Apparatus for collecting body liquids from a patient, comprising:

a reservoir;

means on said reservoir connectable to a patient for collection of patient body liquids in said reservoir;

means for venting air from said reservoir;

a filter in said reservoir and operatively interposed between said venting means and a liquid receiving zone in said reservoir, said filter having a top and a bottom;

means for protecting said filter from contact by liquid in said reservoir prior to filling of said reservoir, despite splashing and other displacement of portions of the liquid in the reservoir from a normal position of rest, said protecting means comprising:

means defining a chamber near the intended maximum liquid height in said reservoir, means for supporting said filter in said chamber and in spaced relation from top and bottom walls of said chamber and for positively preventing liquid contact with the bottom of said filter, means connecting the bottom of said filter to said venting means for venting air in said reservoir through the top of said filter to the bottom thereof and thence to said venting means, the top of said filter being exposed to receive air from said reservoir, flow restricting means for routing a limited flow of fluid from said reservoir to said chamber while directing liquid away from the exposed top of said filter.

2. The apparatus of claim 1 in which said reservoir has a cover, said means for protecting said filter comprising a substantially horizontal deck defining the top wall of said chamber and spaced above said filter, said filter supporting means including means upstanding from said deck and fixedly pendently supporting said deck from said cover in vertically spaced relationship thereto, a boss upstanding from said deck and spaced below said cover, said flow restricting means comprising a through hole extending down through said boss and deck and communicating from the space above said deck down into said chamber, the space above the deck communicating with the interior of the reservoir for venting air therefrom.

3. The apparatus of claim 2 in which said through hole enters the chamber at a location radially outboard of said filter so that fluids entering the chamber through the through hole do not fall on the input face of the filter.

4. The apparatus of claim 3 including a barrier extending down from said deck at least to the level of said filter and radially interposed between the filter and through hole to positively block any straight line travel of fluids leaving said through hole towards said filter.

5. Apparatus for collecting body liquids from a patient, comprising:

a reservoir;

means on said reservoir connectable to a patient for collection of patient body liquids in said reservoir;

means for venting air from said reservoir;

a filter in said reservoir and operatively interposed between said venting means and a liquid receiving zone in said reservoir;

means for protecting said filter from contact by liquid in said reservoir prior to filling of said reservoir, despite splashing and other displacement of portions of the liquid in the reservoir from a normal position of rest, said protecting means comprising:

means defining a chamber near the intended maximum liquid height in said reservoir, means for supporting said filter in said chamber and in spaced relation from top and bottom walls of said chamber and for blocking liquid contact with the bottom of said filter, means connecting the bottom of said filter to said venting means for venting air in said reservoir through said filter to said venting means, the top of said filter being exposed to receive air in said chamber, flow restricting means for routing a limited flow of fluid from said reservoir to said chamber while directing liquid away from the open top of said filter, said filter supporting means comprising an upward opening bowl having a bottom wall spaced above the bottom wall of the chamber to define a liquid collection sump therebetween, said bowl having a peripheral wall upstanding from the bowl bottom wall, the filter lying in said bowl, the bowl peripheral wall extending above the filter and being spaced below the top wall of said chamber, such that sufficient liquid must collect in the sump and rise to a level above the peripheral wall of the bowl before said liquid can contact the filter.

6. Apparatus for collecting body liquids from a patient, comprising:
a reservoir;
means on said reservoir connectable to a patient for collection of patient body liquids in said reservoir;
means for venting air from said reservoir;
a filter in said reservoir and operatively interposed between said venting means and a liquid receiving zone in said reservoir;
means for protecting said filter from contact by liquid in said reservoir prior to filling of said reservoir, despite splashing and other displacement of portions of the liquid in the reservoir from a normal position of rest, said protecting means comprising:
means defining a chamber near the intended maximum liquid height in said reservoir,
means for supporting said filter in said chamber and in spaced relation from top and bottom walls of said chamber and for blocking liquid contact with the bottom of said filter,
means connecting the bottom of said filter to said venting means for venting air in said reservoir through said filter to said venting means, the top of said filter being exposed to receive air in said chamber,
flow restricting means for routing a limited flow of fluid from said reservoir to said chamber while directing liquid away from the open top of said filter, said filter support means comprising a bowl having a bottom wall spaced above the bottom wall of said chamber and a peripheral wall extending out from said bowl bottom wall, the filter being located in said bowl, said bowl peripheral wall extending above the filter, means defining a space between the chamber top wall and the top of said bowl peripheral wall for passing air entering the chamber to the top of the filter for venting through the filter, said space between the chamber bottom wall and bottom wall of said bowl and the extension of said peripheral wall of said bowl above said bowl bottom wall defining a sump for storing any such liquid as may enter the chamber, such that a sufficient quantity of liquid must be stored that its level rises above the bowl peripheral wall before such liquid contacts the filter.

7. The apparatus of claim 6 in which the reservoir has a cover and the top wall of the chamber is spaced below the cover of said reservoir, the space above the top of the chamber being in communication with the reservoir for venting of air from the reservoir into the chamber, said flow restricting means comprising a restrictive orifice opening from said space above said chamber into said chamber near the top of the chamber.

8. The apparatus of claim 7 in which said restrictive orifice is in the top wall of said chamber, means extending above and below the top wall of said chamber respectively (1) preventing entry of liquid in shallow depth on said chamber top wall from flowing into said restrictive orifice and (2) preventing liquid from said restrictive orifice from traveling directly into contact with said filter.

9. The apparatus for collecting body liquids from patients, comprising:
a reservoir;
means on said reservoir connectible to a patient for collecting body liquids therefrom in said reservoir;
means for venting air from said reservoir;
a filter in said reservoir and interposed between said venting means and a liquid receiving zone in said reservoir;
means for protecting said filter from contact by liquid prior to filling of said reservoir, despite splashing and other displacement of liquid from a normal position of rest, comprising:
means defining a chamber near the intended maximum liquid height in said reservoir,
means for supporting said filter in said chamber and spaced from top and bottom walls of said chamber for blocking liquid contact with the bottom of said filter, the bottom of said filter being in communication with said venting means for venting air in the reservoir to the filter to the venting means, the top of the filter being exposed to receive air in said chamber,
bowl means having a bottom wall spaced above the chamber bottom wall and a peripheral wall above the filter, said filter being supported in said bowl,
means defining a space between the chamber top wall and the top of the bowl peripheral wall for passing air entering the chamber to the top of the filter.

10. The apparatus of claim 9 including a restrictive orifice through the chamber top wall for routing a limited flow of fluid from the reservoir to the chamber and means above and below the chamber top wall for impeding flow to and from said restrictive orifice to minimize contamination of the top of said filter by liquids from the reservoir.

11. Apparatus for collecting body liquids from a patient, comprising:
a reservoir in which body liquids are to be collected said reservoir having a cover;
means on said reservoir connectible to a patient to collect body liquids therefrom;
means for venting air from said reservoir;
a filter in said reservoir and interposed between said venting means and a liquid receiving zone in said reservoir;
means for protecting said filter from contact by liquids prior to filling in said reservoir despite splash and other displacement of liquid from a normal position of rest within said reservoir, comprising:
a deck spaced below but adjacent to the cover of the reservoir,
means supporting said filter in spaced relation below said deck,
a boss upstanding from said deck and means defining an opening high on said boss and extending down through said deck (1) for communicating between said reservoir and the space between said deck and filter and (2) for passing air from said reservoir to said venting means through said filter,
barrier means interposed radially between said opening and said filter for preventing linear movement of the fluid from said opening to said filter.

12. The apparatus of claim 11 in which said opening is a restrictive orifice.

13. Apparatus for collecting body liquids from a patient, comprising:
- a reservoir in which body liquids are to be collected said reservoir having a cover;
- means on said reservoir connectible to a patient to collect body liquids therefrom;
- means for venting air from said reservoir;
- a filter in said reservoir and interposed between said venting means and a liquid receiving zone in said reservoir;
- means for protecting said filter from contact by liquids prior to filling in said reservoir despite splash and other displacement of liquid from a normal position of rest within said reservoir, comprising:
  - a deck spaced below but adjacent to the cover of the reservoir,
  - means supporting said filter in spaced relation below said deck,
  - a boss upstanding from said deck and means defining an opening high on said boss and extending down through said deck (1) for communicating between said reservoir and the space between said deck and filter and (2) for passing air from said reservoir to said venting means through said filter,
  - barrier means interposed radially between said opening and said filter for preventing linear movement of the fluid from said opening to said filter, an upward opening bowl supporting said filter therein with a fluid inlet face of said filter upward facing, said bowl being spaced below said deck, means defining a chamber containing said bowl and filter and a sump below said bowl for collection of liquid entering said chamber through said opening in said deck, said bowl having a peripheral wall rising above said filter, such that liquid access to said filter is blocked until sufficient liquid is collected in said sump as to rise above the peripheral wall of said bowl.

* * * * *